United States Patent [19]

Sellegaard

[11] Patent Number: 5,399,392
[45] Date of Patent: Mar. 21, 1995

[54] METHOD FOR PRESERVING FLOWERS, PARTICULARLY ROSES

[76] Inventor: Lars E. Sellegaard, 9, Domaine du Camp Lauvas - 1575 Route de Valbonne, 06250 Mougins, France

[21] Appl. No.: 187,116

[22] Filed: Jan. 26, 1994

Related U.S. Application Data

[63] Continuation of Ser. No. 828,961, Apr. 6, 1992, abandoned.

[30] Foreign Application Priority Data

Jun. 7, 1990 [EP] European Pat. Off. ............ 90440051

[51] Int. Cl.$^6$ ................................................. A01N 3/00
[52] U.S. Cl. ........................................... 428/24; 427/4
[58] Field of Search .............................. 427/4; 428/24; 47/DIG. 11, 62; 252/383, 384; 71/11, 33, 60; 8/490, 524

[56] References Cited

U.S. PATENT DOCUMENTS

| | | | |
|---|---|---|---|
| 3,607,488 | 9/1971 | Yordán | 427/4 |
| 3,895,140 | 7/1975 | Sheldon et al. | 427/4 |
| 4,243,693 | 1/1981 | Nordh | 427/4 |
| 4,710,394 | 12/1987 | Sellegaard | 427/4 |
| 4,788,085 | 11/1988 | DeLuca | 427/4 |
| 4,828,890 | 5/1989 | Tiedeman et al. | 427/4 |
| 4,979,378 | 12/1990 | Cardin et al. | 427/4 |
| 4,980,194 | 12/1990 | Allison et al. | 427/4 |

FOREIGN PATENT DOCUMENTS 2178294 2/1987 United Kingdom .

OTHER PUBLICATIONS

Derwent Abstract, No. 49302, of JP 405023052A, Feb. 1993, "Preservation of Cut Flower, Apparatus Therefor and Vase".

*Primary Examiner*—Shrive Beck
*Assistant Examiner*—Diana Dudash

[57] ABSTRACT

Method for preserving natural flowers, in which the lower end of the stem of the flower is immersed into a water/glycerol solution of a dry composition comprising mineral salts, citric acid and dyes, characterized in that the flower to be treated is severed from the upper end of its stem so that the remaining section of said stem still connected to the flower is shorter than 5 cm and preferably of about 1 cm so that the path of said solution towards the flower be as short as possible.

10 Claims, No Drawings

METHOD FOR PRESERVING FLOWERS, PARTICULARLY ROSES

This is a continuation of application Ser. No. 07/828,961, filed on Apr. 6, 1992, now abandoned.

In prior patents (F-85 1992 and F-85 16264) the applicant has described a process and a composition for treating plants in view of keeping their aspect and their natural freshness during an extended period of time after being extracted from their natural environment. The process consisted in immersing the newly cut lower portion of the stem of the plant into a specific solution containing a number of mineral salts and of dyes in a mixture of water and glycerol during a given duration and at a given temperature.

This process and this composition were effective in keeping the freshness of many plants and bushes: after treatment the stems and leaves of said plants kept during many months and even years the aspect and the touch of the fresh plants before treatment.

One critical feature of said compositions was its content in citric acid, which was of 4–5%, allowing a proportion of glycerol up to 40% and a treatment temperature of 38°–45%° C., said conditions being more favorable than the conditions of still older known similar processes. However, even with said conditions, this process was still difficult to work in case of some flowers such as roses, having specially delicate petals as well as a fragile structure such as the overall shape and even a transient scent.

The further words of the Applicant have reached to a modification of this process specially adapted to this specific product and more specially to the treatment of roses.

The invention has therefore as a first object a process of the above general nature but adapted to the preservation treatment of fragile flowers and more specifically of roses. It has also for object a dry composition specially adapted to the use in this process and a liquid solution obtained from said composition. It has also for object the flowers the freshness, the aspect and the scent thereof have been preserved by the use of said process, and more specially the roses.

A critical feature of this process is that the path of the solution up to the flower to be treated should be as short as possible, i.e., shorter than 5 cm and preferably of less. To this effect, the flower is severed as high as possible at the upper end of its stem and the small remaining section is immersed into the solution avoiding any contact of the petals with said solution. At the end of the overall treatment as it will be described hereunder, the stem with its leaves, separately treated by the usual process, is connected to the flower through a flued rod or pin, e.g. of plastic.

Another feature of this invention is the dry composition from which the treatment solution is prepared. In fact, the constituents of this composition are similar to those of the prior known compositions, as described in the two French patents mentioned above, but the proportions thereof have been adapted to the specific treatment of roses.

The following table shows said compositions:

| Component | Proportion Ranges % | Preferred Proportion % |
|---|---|---|
| Potassium Nitrate | 25–40 | 30 |
| Sodium Sulphate | 2–6 | 4 |
| Manganese Sulphate monohyd. | 6–10 | 8 |
| Calcium hydrogen Phosphate | 2–6 | 4 |
| Citric Acid | 2–5 | 4 |

At least one of the following dyes making the remaining 30–60%, preferably 50%:

| | |
|---|---|
| Tartrazine | (E 102) |
| Patent Blue | (E 131) |
| Patent Green | (ES 11 or FD & C N° 3) |
| Amaranth Red | (E 123) |
| Quinoline Yellow | (E 104) |
| Sunset Yellow | (E 110) |
| Ponceau 4 R | (E 124) |
| Wool Green | (E 142) |

The treatment solution comprises about 25 g/l of said dry composition into a solvent comprising a mixture water/glycerolin a volume proportion between 75/25 and 55/45.

The process of the invention in its application to roses comprises the following steps:

1. Sever the rose at the upper end of its stem, the remaining section being shorter than 5 cm and preferably of about 1 cm.
2. Immerse said section into the solution, said solution being slowly circulated in a perforated tube serving to support the flower, the temperature of said solution being between 33° and 44° C.
3. Continue said immersion during 3–7 days at an ambient temperature of 22°–28° C. and at an ambient humidity less than 65%.
4. At the end of this period, hang the treated flower upside down during about 4 weeks at an ambient temperature between 20° and 30° C. and a relative humidity less than 60%.
5. Connect the treated flower with a stem, preferably a treated stem with leaves, through a glued rod or pin.

The treated roses fully keep their freshness and their scent during a very long period, of at least one year.

To obtain special visual effects, the stem which is assembled to the treated flower can be itself treated with the same process but using a different dye so as the leaves are of a different color.

It is clear that this process is specially directed to the treatment of roses but can be used for any flowers having preferably strong petals such as those forming the families of MATRICARIA and PROTEA and also different wild flowers of the APIACEAE family.

I claim:

1. A method for preserving natural flowers, the flowers having as well as attached stem, said method comprising severing the stems attached to the flowers such that the stem still connected to the flower is shorter than 5 cm and leaving a severed stem portion, immersing a lower end of the stem connected to the flower in a water/glycerol solution of a dry composition comprising 35–62% by weight mineral salts, 2–5% by weight citric acid and the remainder of said composition being at least one dye, the solution being maintained at a temperature between 33° and 44° C. and the immersion being for 3 to 7 days at an ambient air temperature of between 22° and 28° C. an at an ambient humidity less than 65% and, after immersion, storing the flower upside down for about 4 weeks at an ambient air temperature of between 20° and 30° C. and a relative humidity of less than 60%.

2. Method according to claim 1, in which said dry composition comprises 25–40% by weight of potassium nitrate, 2–6% by weight of sodium sulphate, 6–10% by weight of manganese sulphate monohydrate, 2–6% by weight of calcium hydrogen phosphate and 2–5% by weight of citric acid, and 30–60% by weight comprising at least one dye selected from the group consisting of:

| Tartrazine | (E 102) |
| Patent Blue | (E 131) |
| Patent Green | (ES 11 or FD & C N° 3) |
| Amaranth Red | (E 123) |
| Quinoline Yellow | (E 104) |
| Sunset Yellow | (E 110) |
| Ponceau 4 R | (E 124) |
| Wool Green | (E 142) |

3. Method according to claim 2, in which the treatment solution comprises about 25 g/l of said dry composition dissolved in a mixture of water/glycerol in a proportion between 75/25 and 55/45 by volume.

4. Method according to claim 1, in which the solution is contained in a perforated tube receiving the stem section and in which said solution continually circulates.

5. Method according to claim 1, in which the flower to be treated is a rose.

6. The method according to claim 1, further comprising assembling a preserved flower with the severed stem portion.

7. The method according to claim 6, wherein the severed stem portion is treated by the same method as the flower prior to assembling with the preserved flower.

8. The method according to either claim 6 or 7 wherein the assembly is made by gluing a pin inserted into the stem of the flower and into the severed stem portion.

9. The method according to claim 7, wherein the severed stem portion is treated by a solution containing a different dye from that used for the immersion of the flower.

10. A rose treated by the method of claim 1.

* * * * *